(12) United States Patent
Jenkins (10) Patent No.: US 9,154,867 B2
(45) Date of Patent: Oct. 6, 2015

(54) EARMUFF ENCLOSURE

(75) Inventor: John Jenkins, San Diego, CA (US)

(73) Assignee: Honeywell Safety Products USA, Inc., Smithfield, RI (US)

( * ) Notice: Subject to any disclaimer, the term of this patent is extended or adjusted under 35 U.S.C. 154(b) by 439 days.

(21) Appl. No.: 13/178,322

(22) Filed: Jul. 7, 2011

(65) Prior Publication Data

US 2012/0243700 A1    Sep. 27, 2012

Related U.S. Application Data

(60) Provisional application No. 61/467,917, filed on Mar. 25, 2011.

(51) Int. Cl.
*H04R 25/00* (2006.01)
*H04R 1/10* (2006.01)

(52) U.S. Cl.
CPC ............ *H04R 1/1083* (2013.01); *H04R 1/1008* (2013.01)

(58) Field of Classification Search
CPC ........................... H04R 1/1058; H04R 1/1066
USPC .......................................................... 381/371
See application file for complete search history.

(56) References Cited

U.S. PATENT DOCUMENTS

| | | | |
|---|---|---|---|
| 3,999,020 A * | 12/1976 | Bastiaans et al. | 381/372 |
| 5,970,160 A | 10/1999 | Nilsson et al. | |
| 6,731,771 B2 | 5/2004 | Cottrell | |
| 6,970,571 B2 | 11/2005 | Knorr et al. | |
| 7,245,735 B2 | 7/2007 | Han | |
| 2,853,034 A1 | 12/2010 | Gresko | |
| 2005/0010315 A1 | 1/2005 | Silverman | |
| 2010/0128885 A1 * | 5/2010 | Roos et al. | 381/72 |
| 2011/0064239 A1 * | 3/2011 | Sjoman et al. | 381/72 |

FOREIGN PATENT DOCUMENTS

| | | |
|---|---|---|
| JP | 2003179990 A | 6/2003 |
| WO | WO2009139682 A1 | 11/2009 |

OTHER PUBLICATIONS

Wikipedia; Bass Reflex; http://en.wikipedia.org/wiki/Bass_reflex; Jul. 7, 2011; 4 pages.
Wikipedia; Loudspeaker enclosure; http://en.wikipedia.org/wiki/Loudspeaker_enclosure; 9 pages.
Search Report and Written Opinion of the International Searching Authority; 9 pages; PCT/US11/44313, mailed Nov. 22, 2011.

* cited by examiner

*Primary Examiner* — Joseph Saunders, Jr.
*Assistant Examiner* — James Mooney
(74) *Attorney, Agent, or Firm* — Conley Rose, P.C.; Kristin Jordan Harkins (57) ABSTRACT

Embodiments relate to earmuffs with speakers, and attempt to improve speaker acoustic quality without negatively impacting sound attenuation of the earmuffs. Embodiments may comprise a speaker plate located behind a speaker unit, and typically the speaker plate comprises a recessed portion with a plurality of holes. When the speaker plate is in place behind the speaker unit, it may cause the speaker to be more accurate across a broad range of frequencies without negatively impacting sound attenuation.

20 Claims, 5 Drawing Sheets

EARMUFF ENCLOSURE

CROSS-REFERENCE TO RELATED APPLICATIONS

This application is related as a non-provisional of and claims benefit under 35 U.S.C §119 to U.S. Provisional Patent Application Ser. No. 61/467917 entitled "Earmuff Enclosure" and filed Mar. 25, 2011, which is assigned to the Assignee of the present application and hereby incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD

Disclosed embodiments relate generally to earmuffs and/or headphones, and more specifically to earmuffs that provide sound attenuation (attenuating external sounds, typically for hearing protection or sound isolation, for example) and that have speakers (allowing for electronic sound reproduction, for example).

BACKGROUND

Given physical constraints, headphone design is typically a study in compromise. This means that at each distinct price point, headphones generally have to balance the conflicting goals of speaker performance and sound attenuation. One way to address this problem might be to use a more expensive speaker to improve speaker performance without negatively impacting the sound attenuation qualities of the earmuff, but this would result in headphones that are too expensive for average consumers (i.e. change the price point). A more typical compromise is to use a standard, less expensive speaker with good mid-range but weak high and/or low frequency response in conjunction with standard headphone sound attenuation. This approach might provide for adequate sound attenuation of external sounds (for hearing protection and/or sound isolation), but the sound quality produced by the headphones would not he particularly good. Applicants are seeking to provide another option, which uses improved design to provide good sound attenuation while also providing quality speaker performance for a moderate price range that rivals that of high-end expensive speakers.

SUMMARY

In one aspect, the disclosure may include a device Which may comprise an earmuff with sound attenuating material; a speaker having a diaphragm; and a speaker plate located behind the speaker unit. In embodiments, the speaker plate may comprise a recessed portion and one or more holes in the recessed portion, wherein the speaker seals with the speaker plate to form a chamber behind the speaker unit. Additionally, embodiments may include a foam ring located behind the speaker plate, and having a hollow cavity space in communication with the chamber via the holes. Embodiments may also have a foam block closing the end of the foam ring opposite the speaker plate. Embodiments may also isolate the chamber and the hollow cavity from the outside ambient surrounding environment so that there is substantially no airflow between the outside ambient surrounding environment and either the hollow cavity and the chamber.

In other aspects, an earmuff might comprise: a 30-35 mm mylar film speaker; a speaker plate, having a recessed portion and a plurality of holes in the recessed portion each having a diameter of about 1 mm; a reticulated foam ring, having a hollow cavity space; a reticulated foam block; and a non-reticulated moulded foam; wherein the speaker fits over the recessed portion of the speaker plate to form a chamber; the plurality of holes allow air flow between the chamber and the hollow cavity space; and the moulded foam isolates the chamber and the hollow cavity space so there is substantially no air flow with an outside ambient surrounding environment. And yet in other aspects, an earmuff might comprise a 30-35 mm mylar film speaker unit; a speaker plate, having a recessed portion and a lip; a reticulated foam ring, having a hollow cavity space; a reticulated sound attenuating foam material; a non-reticulated moulded foam; and a shell; wherein: the speaker unit comprises a diaphragm, a magnet, and a casing, wherein the casing has an open front and a closed rear and wherein the rear of the casing comprises one or more open apertures; the speaker plate comprises one or more holes in the recessed portion; the speaker sits atop the lip of the speaker plate so that the recessed portion of the speaker plate forms a chamber; the foam ring is located between the speaker plate and the sound attenuating foam material; the speaker unit, speaker plate, foam ring, and sound attenuating foam material are located within the shell of the earmuff; and the non-reticulated moulded foam substantially fills any remaining space within the shell of the earmuff.

Embodiments may include having the chamber and the hollow cavity space in communication via the one or more holes; having the one or more holes provide an opening of between about 0.7-8.0 square millimeters; and/or having the foam ring and the sound attenuating foam material each comprise reticulated polyurethane foam. In other embodiments, the chamber and the hollow cavity may not be in communication with the outside ambient surrounding environment. And in still other embodiments, the non-reticulated moulded foam may seal the earmuff to isolate the chamber, the hollow cavity space, and an airspace in the speaker unit between the diaphragm and the rear of the casing.

BRIEF DESCRIPTION OF THE DRAWINGS

For a more complete understanding of the present disclosure, and for further details and advantages thereof, reference is now made to the accompanying drawings, in which.

DETAILED DESCRIPTION

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or have a characteristic, that particular component or feature is not required to be included or to have the characteristic.

Disclosed embodiments relate to earmuffs with speakers, and attempts to improve speaker acoustic quality without negatively impacting sound attenuation of the earmuff. Typically, a speaker plate having a recessed portion and one or more holes in the recessed portion might seal with the speaker to form a chamber behind the speaker unit. In some embodiments, the hole(s) in the speaker plate would allow air in the chamber to interact with a larger controlled volume of air, typically behind the speaker plate. This arrangement may cause the speaker to perform better (providing a more accurate or flat response across audible frequencies), without negatively impacting the sound attenuation that the earmuffs provide for external sounds. So the disclosed embodiments attempt to provide an improvement in the balancing of the two key properties of an audio earmuff—sound attenuation and speaker acoustic quality.

Figure 1:
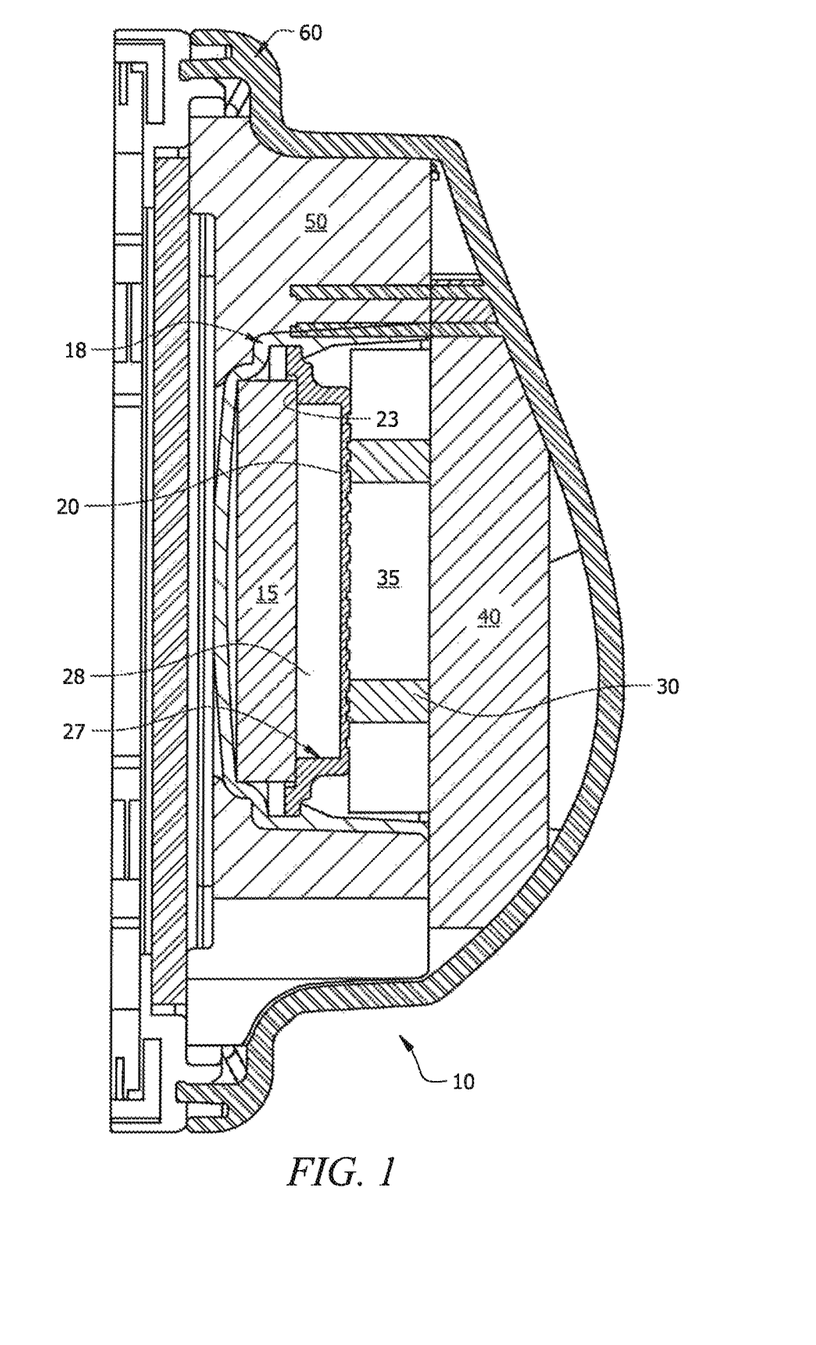
FIG. 1 is a cross-section diagram of one embodiment of the improved earmuff.

In the embodiment of FIG. 1, the speaker plate 20 has a recessed portion 27 (typically about 5 mm deep) and one or more holes 25 in the recessed portion 27. While the holes 25 could be located anywhere on the recessed portion 27, in FIG. 1 the holes 25 are located in the base of the speaker plate (distally away from the speaker unit 15). The speaker unit 15 (typically a 30-35 mm mylar film speaker) fits snuggly atop the recessed portion 27 in the speaker plate 20 to form a seal, thereby creating an enclosure or chamber 28 of air behind the speaker unit 15. More specifically, in FIG. 1 the speaker unit 15 fits into a lip or rim 23 (slightly recessed and typically having a width of about 1-2 mm, to provide a good fit between the speaker and the speaker plate), so that when the speaker 15 rests on the lip 23, the recessed portion 27 forms a volume chamber 28 of air. The speaker plate 20 is typically designed to form a specific volume of air behind the speaker 15. Thus, the speaker plate 20 is typically sufficiently thick and of sufficiently rigid material so that it will not flex significantly during operation of the speaker 15. In the embodiment of FIG. 1, the speaker plate 20 is formed from a stiff, high strength plastic material, such as polyoxymethylene (POM), and has a thickness of between about 1-2 mm. The rigidity of the speaker plate 20 defines a set volume of air space within the chamber 28 directly behind the speaker unit 15 (with the air space enclosed between two hard/stiff surfaces, in this case the rear of the speaker unit 15 and the speaker plate 20). The holes 25 in the recessed portion of the speaker plate control the amount of air drawn into and/or out of the chamber 28 by allowing communication/interaction with a contained larger volume of air behind the speaker plate 20.

In FIG. 1, the base/rear or back side of the speaker plate recessed portion 27 contacts a foam ring 30. While any foam might be used for the foam ring 30, h the embodiment of FIG. 1, the foam ring 30 is formed of reticulated foam, preferably reticulated polyurethane foam. The foam ring 30 of FIG. 1 has walls of foam about 10 mm thick, with the outer diameter of the foam ring being about 50 mm and the inner diameter (i.e. the diameter of the hollow space/cavity of the foam ring) being about 25-27 mm. The depth of the foam ring 30 of FIG. 1 is about 10 mm. The hollow space 35 (cavity) in the foam ring 30 defines a second air chamber located behind the speaker plate 20 (which in this embodiment is a larger, controlled volume of air space). This hollow space 35 is typically larger in volume than the chamber 28 between the speaker 15 and the speaker plate 20. While embodiments typically have a hollow space 35 that is at least about 15% larger than the chamber 28, more often the hollow space 35 would be between about 2-6 times as large as the chamber 28. In the embodiment of FIG. 1 the hollow space 35 is about twice as large. And while the foam ring 30 in FIG. 1 is a circular tube of foam, embodiments may have any hollow foam shape so long as it defines a sufficiently large hollow space/cavity.

The foam ring 30 of FIG. 1 then contacts a block of sound attenuating foam 40 (which might be cut reticulated foam). The sound attenuating foam 40 may be any shape, so long as it can effectively cap the hollow space 35 of the foam ring 30 (to form a closed chamber). The sound attenuating foam 40 typically is sufficiently thick to prevent echoes, and in the embodiment of FIG. 1, the foam block is about 9-12 mm thick, and has a surface area sufficiently large to support the entire foam ring 30. In the embodiment of FIG. 1, reticulated polyurethane foam is typically used for the foam ring 30 and the foam block 40, since the material is effective at absorbing sound to prevent echoing within the earmuff 10. And in FIG. 1, non-reticulated moulded foam 50 typically fills the hulk of the remaining space in the earmuff shell or cup 60, surrounding the speaker 15 (except on its inward-facing side), speaker plate 20, and foam ring 30, and abutting the block of foam 40. This moulded foam 50 helps to hold the speaker unit 15 in place and fills the empty volume in the earmuff 10, thereby reducing echoes to improve speaker sound quality. Furthermore, in the embodiment of FIG. 1 this non-reticulated (closed-cell) moulded foam 50 serves to effectively seal the air space within the earmuff behind the speaker, so that there can be no communication with the outside ambient air surrounding the earmuff 10. In other words, the non-reticulated moulded foam 50 isolates the air space within the earmuff behind the speaker diaphragm.

Figure 2A:
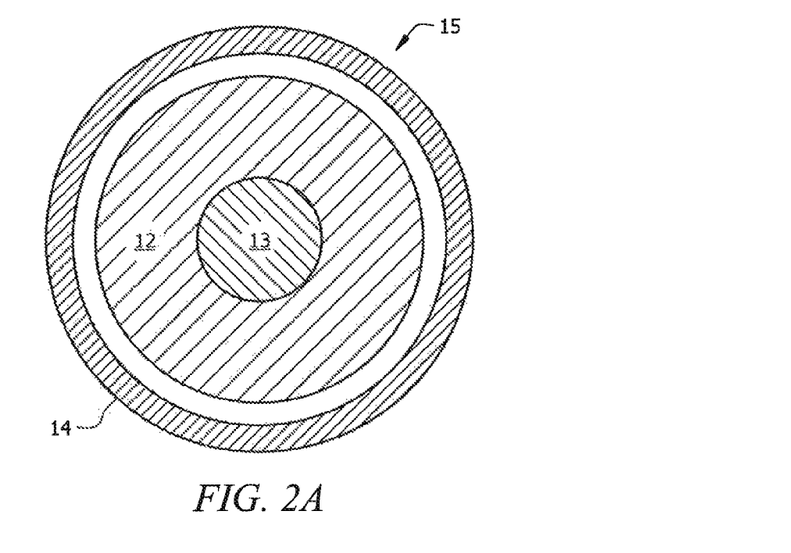
FIGS. 2A-2C illustrate an exemplary embodiment of a speaker unit that may be used in an improved earmuff, with FIG. 2A showing a plan view of the front (inward-facing side) of the speaker unit, FIG. 2B showing a plan view of the rear (outward-facing side) of the speaker unit, and FIG. 2C showing a cross-section view of the speaker unit (as indicated by the 2C cross-section notation in FIG. 2B)
Figure 2B:
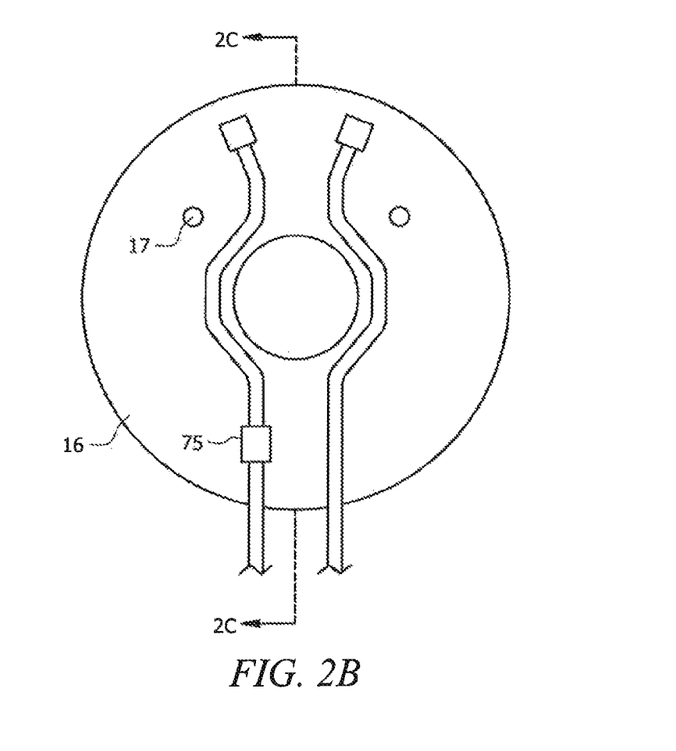
Figure 2C:
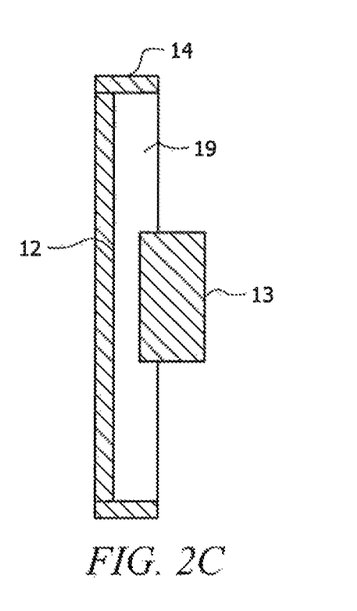

FIGS. 2A-2C illustrate a typical exemplary speaker unit 15 of the sort that might be used in the earmuff of FIG. 1. Typically, an off-the-shelf speaker unit would be used, such as a 30-35 mm mylar film speaker for example. The speaker 15 has a film/diaphragm 12 and a magnet 13 for producing sounds based on electrical signals. The diaphragm 12 and magnet 13 are located in a casing 14. In the embodiment of FIG. 2, the casing 14 is open on its front/inward-facing surface (to allow sound created by movement of the diaphragm 12 to exit towards the user's ear) and has a hard/solid rear surface 16 with one or more open apertures 17 in it. An air space 19 is thus formed between the diaphragm 12 and the rear of the casing 14. These open apertures 17 in the casing 14 allow airflow into and/or out of the speaker 15. Thus, in operation the embodiment of FIG. 1 may have airflow between the airspace 19 in the speaker 15 and the chamber 28 of the speaker plate 20 (through apertures 17) and between the chamber 28 and the hollow space 35 of the foam ring (via holes 25). It should be noted, however, that there is no air flow communication with the outside air, since the non-reticulated moulded foam 50 serves to seal the earmuff from the outside air. In the embodiment of FIG. 1, it is important that the entire air volume behind the speaker diaphragm 12 (including the air space 19 in the speaker unit between the diaphragm 12 and the rear wall 16 of the casing, the air chamber 28 between the rear 16 of the speaker unit and the speaker plate 20, and the hollow space 35 of the foam ring 30) is sealed to form a closed/set/fixed volume of air, since it is believed that this helps improve speaker accuracy.

In FIG. 1, speaker bracket 18 may also be used to securely seat the speaker 15 in the lip 23 atop the recess of the speaker plate 20, and to help hold the speaker 15 in place in the earmuff 10 (typically by fitting snuggly in the moulded foam). Preferably, the volume of air space behind the speaker plate 20 would not have anything located in it that would resonate (since that would reduce NRR and make the earmuff less effective for sound attenuation or isolation). Alternatively, resonance in this space would be minimized by only having electrical wires from the input jack located therein, and typically those wires would be coated to reduce resonance. Additionally, the speaker 15 may not be rigidly attached to the shell 60 of the earmuff. Rather, the speaker assembly 15 may be held in place in the earmuff 10 by the moulded foam 50, further reducing resonance that could reduce NRR. And in some embodiments, air flow control in the cushion of the earmuff (not shown in FIG. 1, but typically located on the inward-facing side of the earmuff 10 and fitting snuggly up against the user's head to seal the earmuff) may be used to help ensure that this design does not negatively impact sound attenuation for external sounds. U.S. Pat. No, 5,970,160, hereby fully incorporated by reference for all purposes to the extent that it does not conflict with details herein, provides additional information about such air flow control cushions. The entire assembly of speaker, speaker plate, and sound attenuating material is enclosed within the shell 60 of the earmuff.

Figure 3:
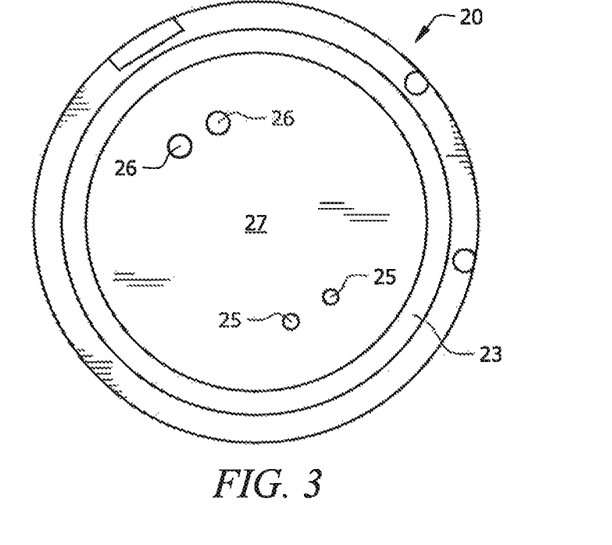
FIG. 3 illustrates one embodiment of an exemplary speaker plate of an improved earmuff.

FIG. 3 illustrates an embodiment of the speaker plate 20. Embodiments may typically use a speaker plate 20 with a recessed portion 27 between about 3-10 mm in depth (so that the chamber 28 of air directly behind the speaker diaphragm 12 is sized to have a diameter slightly smaller than that of the speaker 15, and a depth of between about 3-10 mm). Embodiments may also typically use a number and size of open holes 25 (i.e. holes without wires or other obstructions) in the speaker plate 20 selected to provide between about 0.7-8.0 square mm of open surface area in the base of the recessed portion 27 of the speaker plate, allowing for adequate air flow between the speaker plate chamber 28 and the hollow space 35 in the foam ring 30. More preferably, the surface area of openings in the speaker plate recess would be between about 1.5-3 square millimeters. Typically, the holes 25 are approximately circular and have a diameter of about 1 mm (although other shapes and sizes of holes may be used in some embodiments), and in some embodiments the holes 25 may be tapered. In the embodiment of FIG. 3, the holes 25 are tapered on the inside surface of the speaker plate 20 (toward the speaker 15), but are not tapered on the outside surface of the speaker plate 20 (toward the foam ring 30). The taper might be defined by a small radius, such as a radius of about 0.1 mm. Alternatively both sides, either side, or neither side of the holes could be tapered. And while the embodiment of FIG. 3 has two open holes 25 in the base of the speaker plate recessed portion (with two other, closed holes 25 that are ultimately filled by wires leading from the speaker 15 to an input jack for audio input signal, and typically sealed with an adhesive or other sealant to minimize airflow therethrough), other embodiments might have between 1 and 10 open holes. In designing the open holes 25 in the speaker plate 20, the total surface area of the open hole(s) 25 should typically be sufficient to allow needed air flow between the speaker plate air chamber 28 and the hollow space 35 in the foam ring, but should not typically be so great that the two chambers acoustically act effectively as one large chamber (i.e. as if there were no base to the speaker plate).

In the specific embodiment shown in FIG. 3, there are two open holes 25 of about 1 mm diameter in the speaker plate 20. In FIG. 3, this embodiment has a space of about 5 mm between the open holes 25. The holes 25 are typically located on the base of the recessed portion of the speaker plate so that the holes 25 open into the hollow space 35 of the foam ring (providing communication of air between the chamber 28 of the speaker plate and the hollow space 35 of the foam ring). In the embodiment of FIG. 3, the open holes 25 are located nearer the wall of the foam ring (although other hole location and spacing may also be effective for other embodiments). FIG. 3 also has two other holes 26, but when the speaker plate is installed in the earmuff, these holes 26 are blocked by wires (for providing he electrical signals to the speaker). In FIG. 3, the wires are held in place by a silicone adhesive, which also seals the holes 26 (so that only the two open holes 25 allow air flow between the speaker plate air chamber 28 and the hollow space 35 in the foam ring). The design of FIG. 1 typically improves the accuracy of the speaker 15 across a range of frequencies, allowing a standard speaker to perform better, especially in the high and low frequencies. And the design typically improves speaker performance without negatively impacting the sound attenuating qualities of the earmuff. Typically, the earmuff of FIG. 1 would provide about 25 Noise Reduction Rating, although other embodiments may provide varying NRR depending on such features as the size of the earmuffs, the air volume within the earmuffs, and the amount and type of sound reducing/absorbing/blocking material (such as foam) within the earmuff.

So in the embodiment of FIG. 1, the air in the chamber 28 is a calculated volume, and the holes 25 in the recessed portion of the speaker plate allow for better control over movement of the speaker 15. It is believed that the air volume directly behind the speaker acts as acoustic resistance, like a spring pulling on the diaphragm of the speaker (and the precise spring rate depending on the size of the chamber, temperature of the air, etc.). The holes in the recessed portion 27 of the speaker plate make that spring effect weaker (by allowing communication with the larger closed volume of air in the hollow space 35 behind the speaker plate 20). Thus, the number, size, and geometry of the holes, along with the volume of the chamber and perhaps the volume within the hollow space of the foam ring, determine the strength of the spring effect pulling on the speaker diaphragm. The volume of air behind the speaker plate 20 (for example, within the foam ring 30 of FIG. 1) should typically be larger than that contained within the chamber 28. This provides a reservoir of air to interact with the chamber 28 (so that air can flow readily into the chamber 28 as needed), and also helps sound attenuation (since earmuffs tend to perform better attenuating sound by maximizing free air space). In this way, the design may improve the high and low frequency response to provide improved accuracy across the frequency range. The embodiment of FIG. 1, for example, typically might have better frequency response in the lower range (of about 20-200 Hz, for example) and/or in the higher voice range (of about 2000-4000 Hz, for example).

Figure 4:
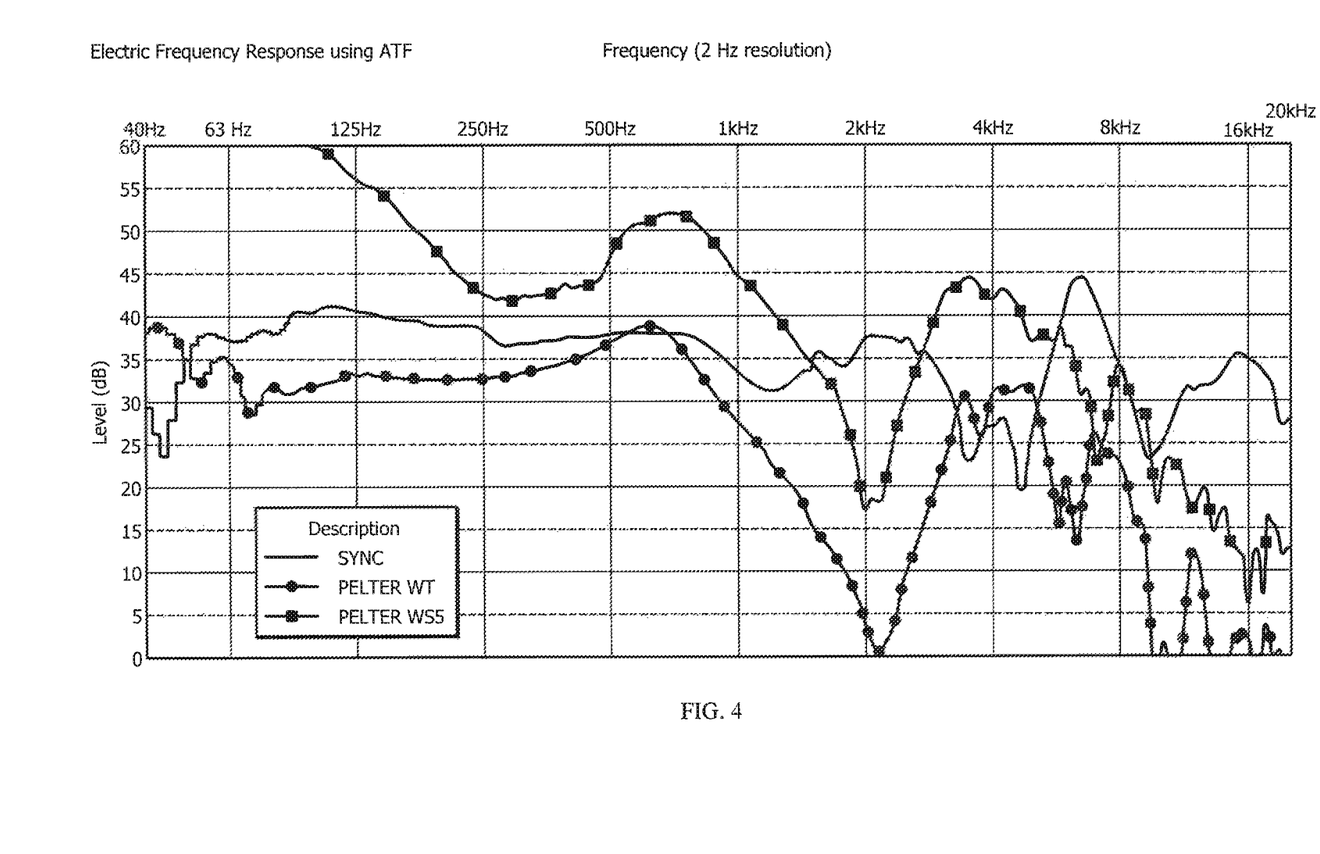
FIG. 4 illustrates test data showing that the embodiment of FIG. 1 has better speaker performance than similar competitor models.
Figure 5:
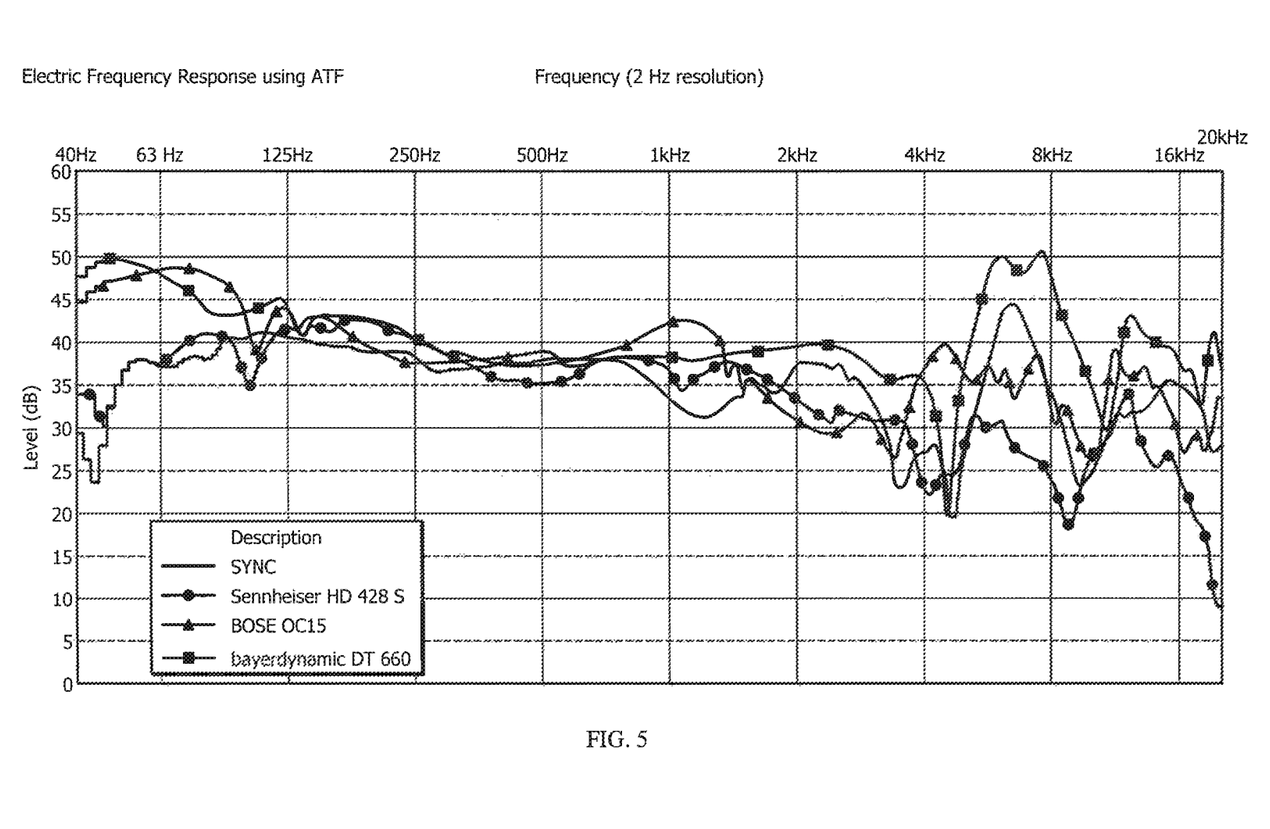
FIG. 5 illustrates test data showing that the embodiment of FIG. 1 performs comparably to higher-end competitor models sold at a much higher price point.

Frequency charts shown in FIGS. 4 and 5 may help to illustrate the improved speaker accuracy provided by disclosed embodiments. FIG. 4 shows the improved speaker accuracy of the embodiment of FIG. 1 (designated SYNC) compared to comparably priced competitor models (using similar 35 mm mylar film speakers, for example), while FIG. 5 illustrates how the tested model of the embodiment of FIG. 1 (designated SYNC) compares favorably to the speaker accuracy of much higher priced competitor models (using higher-end non-mylar film speakers). For the tests depicted in these charts, pink noise was played on the speakers in accordance with industry standards. In evaluating accuracy, a flatter line typically indicates more accuracy. FIG. 4 for example, shows that for the embodiment of FIG. 1 the lower frequencies stay flatter significantly longer than competitor earmuffs using similar speakers. And FIG. 5 shows that the earmuff of FIG. 1 using a standard speaker (with a cost of probably around $35) produced sound quality approximately on par with competitor products that cost upward of $200.

Embodiments might also feature a volume manager 75 on the speaker input/output. This might be resistance in the circuitry designed to lower the maximum volume to safe levels (so that a user could listen at maximum level for 8 hours without hearing damage, for example). So for example, the maximum volume output by the earmuffs might be lowered to about 82-85 dB. Since the invention provides for better speaker sound quality (especially in conjunction with good attenuation of external sounds), the users should not need to listen at dangerously high levels. Rather, they will be able to hear subtle sound variations produced by the speakers without having to play sounds at excessive levels. Thus, users may enjoy a safe sound level, without negatively impacting the user's ability to discern subtle sounds, since the improved speaker performance better handles such subtle sounds (especially when background noise is reduced due to the earmuff's sound attenuating properties). Such a volume manager 75 may be integrated/housed with the shell 60, or it may be located externally.

The disclosed earmuffs may be used for audio/music play (such as personal music devices or mp3 players, for example), or may be used for communication (such as for mobile or cell phones, for example). The earmuff may be worn for leisure (such as listening to music), or may be used as hearing protection on a worksite (providing workers with the option for improved communication and/or entertainment during the work day). Embodiments may include earmuffs equipped with a pair of speakers (typically joined by a headband) and a 3.5 mm or other input jack, allowing the earmuffs to be used as headphones with portable audio devices (such as MP3 players and cellular telephones). Typically, no batteries are needed, since the speakers would be powered by the portable device itself in such configurations.

Embodiments of the earmuff 10 are typically made by forming a hollow shell for the cup of the earmuff, a speaker plate having a recessed portion with one or more holes (and the speaker plate optionally also having a lip), a block of reticulated foam, a ring of reticulated foam, and a moulded foam piece, typically formed from non-reticulated foam. The moulded foam piece would be shaped with an opening therethrough of the size and shape to allow for snug seating of the speaker, speaker plate, and foam ring, and would also be sized and shaped to substantially fill any open or empty space/volume in the earmuff cup. And in some embodiments, the moulded foam would also have another opening for any wire(s) coming from the input jack to the speaker. A speaker unit may either be manufactured or purchased off-the-shelf. Sound attenuating material, typically the block of reticulated foam, is placed in the bottom of the hollow space in the shell (so it would be outward-facing in use). The speaker unit, speaker plate, and foam ring may be placed inside the opening in the non-reticulated moulded foam that is shaped for a snug lit, and optionally may be held in place by a speaker bracket. The assembly of the moulded foam along with the speaker, speaker plate, and foam ring may be placed in the hollow space of the shell atop the block of reticulated foam, at which point the upper/inner surface area of the hollow space in the earmuff shell should be substantially estantially filled. A dust cover may be placed atop the moulded foam and speaker on the inner surface of the earmuff cup. An air flow control cushion may be attached to the inner surface of the earmuff cup as the inner-most layer for making contact with a user's head. And in some embodiments, two such earmuff cups might be attached via a headband, which would typically be adjustable to allow for a customized fit for each specific user.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided, for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field of Invention," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive. Reference in the disclosure to inner or outer may be made for purposes of description, with "out" or "outer" typically meaning away from the user's eardrum, and "in" or "inner" typically meaning towards the user's eardrum.

What is claimed is:

1. An earmuff comprising:
a 30-35 mm mylar film speaker unit;
a speaker plate, having a lip and a recessed portion with a base;
a reticulated foam ring, having a hollow cavity space with an open volume of air;
a reticulated sound attenuating foam material;
a non-reticulated moulded foam; and
a shell;
wherein:
the speaker unit comprises a diaphragm, a magnet, and a casing, wherein the casing has an open front and a closed rear, wherein the rear of the casing comprises one or more open apertures, and wherein an air space is formed between the diaphragm and the casing;
the speaker plate comprises one or more open holes in the recessed portion;
the speaker sits atop the lip of the speaker plate so that the recessed portion of the speaker plate forms a first chamber between the rear of the casing of the speaker and the base of the recessed portion of the speaker plate;
the foam ring is located behind the speaker plate and between and in contact with the speaker plate and the sound attenuating foam material, such that the hollow cavity space within the ring forms a second chamber between the base of the recessed portion of the speaker plate and the sound attenuating foam material;
the one or more open holes in the recessed portion of the speaker plate open into the hollow cavity space of the foam ring;
the speaker unit, speaker plate, foam ring, and sound attenuating foam material are located within the shell of the earmuff; and
the non-reticulated moulded foam substantially fills any remaining space within the shell of the earmuff.

2. The earmuff of claim 1 wherein the first chamber and the hollow cavity space are in communication via the one or more open holes; wherein the one or more open holes provide between 1.5-3.0 square millimeters of open surface area; and wherein the foam ring and the sound attenuating foam material each comprise reticulated polyurethane foam.

3. The earmuff of claim 2 wherein the first chamber and the hollow cavity are not in air flow communication with an outside ambient surrounding environment.

4. The earmuff of claim 3 wherein the non-reticulated moulded foam seals the earmuff to isolate the first chamber, the hollow cavity space, and an air space in the speaker unit between the diaphragm and the rear of the casing.

5. The earmuff of claim 4 wherein the hollow cavity space is between 15% larger and 2 times larger than the first chamber.

6. An earmuff comprising:
sound attenuating material;
a speaker having a diaphragm and a casing, forming an air space between the diaphragm and the casing;
a speaker plate located behind the speaker; and
a ring located behind the speaker plate and between the speaker plate and the sound attenuating material;
wherein the speaker plate comprises a recessed portion with a base and one or more holes in the recessed portion, and wherein the speaker seals with the speaker plate to form a chamber between the speaker and the base of the recessed portion of the speaker plate; and
wherein the sound attenuating material is located behind the speaker plate; and
wherein the rim comprises a hollow cavity between the speaker plate and the sound attenuating material, wherein the ring is composed of foam, and wherein the hollow cavity has volume larger than that of the chamber.

7. The earmuff of claim 6 wherein sound attenuating material comprises reticulated polyurethane foam, and wherein the earmuff provides at least 25 NRR.

8. The earmuff of claim 6 further comprising a volume manager on the speaker input.

9. The earmuff of claim 8 wherein the volume manager comprises resistance in the circuitry of the speaker input; and wherein the volume manager limits the maximum volume output for the speaker to 82 dB.

10. The earmuff of claim 6 wherein the recessed portion of the speaker plate has a depth of between 3-10 mm.

11. The earmuff of claim 6 wherein the speaker is a 30-35 mm mylar film speaker.

12. The earmuff of claim 6 wherein both the sound attenuating material and the foam ring comprise reticulated foam; and wherein the one or more holes have an open surface area of between 0.7-8.0 square millimeters.

13. The earmuff of claim 12 wherein the chamber and the hollow cavity are isolated from an outside ambient surrounding environment so that there is substantially no airflow between the outside ambient surrounding environment and either the hollow cavity or the chamber.

14. The earmuff of claim 6 wherein the hollow cavity of the ring has a diameter of about 25-27 mm and a depth of about 10 mm, and the hollow cavity is centered on a longitudinal axis of the ring.

15. The earmuff of claim 6 wherein all air space behind the speaker diaphragm is sealed to prevent air flow communication with outside ambient surrounding environment.

16. The earmuff of claim 6 wherein the one or more holes in the recessed portion of the speaker plate open into the hollow cavity of the ring.

17. The earmuff of claim 16 wherein the hollow cavity forms a second chamber in air flow communication with the chamber of the speaker plate through the holes in the recessed portion of the speaker plate.

18. An earmuff comprising:
a 30-35 mm mylar film speaker comprising a diaphragm and a casing, with an air space located between the diaphragm and a rear portion of the casing;
a speaker plate, having a recessed portion with a base and a plurality of open holes in the recessed portion each having a diameter of 1 mm;
a reticulated foam ring, having a hollow cavity space with an open volume of air;
a reticulated foam block; and
a non-reticulated moulded foam;

wherein the speaker fits over the recessed portion of the speaker plate to form a first chamber located behind the speaker between the speaker and the base of the recessed portion of the speaker plate; the foam ring is located behind the speaker plate between the base of the recessed portion of the speaker plate and the foam block; the plurality of holes in the speaker plate open into the hollow cavity space of the foam ring and allow air flow between the first chamber and a second chamber formed by the hollow cavity space located between the base of the recessed portion of the speaker plate and the foam block; and the moulded foam isolates the first chamber and the second chamber so there is substantially no air flow with an outside ambient surrounding environment.

19. The earmuff of claim 18 wherein the first chamber has a depth between 3-10 mm; and the second chamber has a volume between 2-6 times that of the first chamber.

20. The earmuff of claim 19 further comprising an air flow control cushion, wherein the earmuff provides at least 25 NRR.

* * * * *